United States Patent
Vial et al.

(10) Patent No.: US 10,058,436 B2
(45) Date of Patent: Aug. 28, 2018

(54) RADIOPAQUE MARKER FOR BIORESORBABLE STENTS

(71) Applicant: Arterial Remodeling Technologies, S.A., Noisy le Roi (FR)

(72) Inventors: Beatrice Vial, Chargey les Gray (FR); Machiel van der Leest, Paris (FR)

(73) Assignee: ARTERIAL REMODELING TECHNOLOGIES SA (FR)

( * ) Notice: Subject to any disclaimer, the term of this patent is extended or adjusted under 35 U.S.C. 154(b) by 100 days.

(21) Appl. No.: 14/438,377

(22) PCT Filed: Oct. 24, 2013

(86) PCT No.: PCT/EP2013/072239
§ 371 (c)(1),
(2) Date: Apr. 24, 2015

(87) PCT Pub. No.: WO2014/064180
PCT Pub. Date: May 1, 2014

(65) Prior Publication Data
US 2015/0272751 A1 Oct. 1, 2015

Related U.S. Application Data

(60) Provisional application No. 61/718,532, filed on Oct. 25, 2012.

(51) Int. Cl.
*A61L 31/18* (2006.01)
*A61F 2/82* (2013.01)
(Continued)

(52) U.S. Cl.
CPC ............... *A61F 2/82* (2013.01); *A61F 2/915* (2013.01); *B29C 65/02* (2013.01);
(Continued)

(58) Field of Classification Search
CPC .... A61F 2/91; A61F 2250/0098; A61F 2/915; A61F 2220/0066; A61F 2230/0013;
(Continued)

(56) References Cited

U.S. PATENT DOCUMENTS

| 5,725,572 A | 3/1998 | Lam et al. |
| 6,174,330 B1 | 1/2001 | Stinson |

(Continued)

FOREIGN PATENT DOCUMENTS

| EP | 0894481 | 5/2005 |
| EP | 1974701 | 10/2008 |

(Continued)

OTHER PUBLICATIONS

Definition of embed. Retrieved from http://www.dictionary.com/browse/embed (May 16, 2017).*

(Continued)

*Primary Examiner* — Seema Mathew
(74) *Attorney, Agent, or Firm* — Tarolli, Sundheim, Covell & Tummino LLP

(57) ABSTRACT

The present patent application relates to a method of applying a radiopaque marker to a tubular stent. A radiopaque marker for a tubular stent is constructed of a radiopaque material and configured with a roof portion and a pair of wall portions extending approximately perpendicular to the roof portion. The radiopaque marker is applied to a tubular stent by a method including the steps of forming the tubular stent with a pair of openings through a wall of the tubular stent; inserting the wall portions of the radiopaque marker into the openings in the wall of the tubular stent; and heat treating the tubular stent to retain the wall portions of the radiopaque marker within the openings in the wall of the tubular stent. The heat treating step also embeds the roof portion of the radiopaque marker onto the wall of the tubular stent. The (Continued)

method of the invention is particularly adapted for applying a radiopaque marker to a bioresorbable polymeric vascular stent.

8 Claims, 6 Drawing Sheets

(51) Int. Cl.
*A61F 2/915* (2013.01)
*B29C 65/02* (2006.01)
*B29K 696/00* (2006.01)
*B29L 31/00* (2006.01)

(52) U.S. Cl.
CPC .............. *A61F 2002/91575* (2013.01); *A61F 2210/0004* (2013.01); *A61F 2210/0076* (2013.01); *A61F 2230/0054* (2013.01); *A61F 2230/0069* (2013.01); *A61F 2250/0098* (2013.01); *B29K 2696/00* (2013.01); *B29K 2995/006* (2013.01); *B29L 2031/7532* (2013.01)

(58) Field of Classification Search
CPC .. A61F 2002/91541; A61F 2002/91558; A61F 2230/0054; A61F 2250/0067; A61F 2250/0068; A61F 2/82; A61F 2/86; A61F 2250/0097; B29C 35/02; A61L 31/08; A61L 31/18
See application file for complete search history.

(56) References Cited

U.S. PATENT DOCUMENTS

| | | | |
|---|---|---|---|
| 6,293,966 B1* | 9/2001 | Frantzen | A61F 2/91 606/198 |
| 6,334,871 B1* | 1/2002 | Dor | A61F 2/91 623/1.34 |
| 6,368,346 B1 | 4/2002 | Jadhav | |
| 6,464,723 B1 | 10/2002 | Callol | |
| 6,635,082 B1 | 10/2003 | Hossainy et al. | |
| 6,652,579 B1 | 11/2003 | Cox et al. | |
| 6,991,647 B2 | 1/2006 | Jadhav | |
| 7,473,417 B2 | 1/2009 | Zeltinger et al. | |
| 7,553,325 B2 | 6/2009 | Stinson | |
| 7,914,571 B2* | 3/2011 | Calisse | A61F 2/90 623/1.34 |
| 7,951,194 B2 | 5/2011 | Gueriguian et al. | |
| 8,127,422 B2 | 3/2012 | Wu | |
| 8,322,593 B2* | 12/2012 | Wack | A61F 2/915 228/170 |
| 8,721,709 B2* | 5/2014 | Schlun | A61F 2/91 623/1.15 |
| 9,445,924 B2* | 9/2016 | Wolf | A61F 2/915 |
| 2004/0015228 A1* | 1/2004 | Lombardi | A61F 2/91 623/1.18 |
| 2004/0015229 A1* | 1/2004 | Fulkerson | A61F 2/91 623/1.22 |
| 2004/0073291 A1* | 4/2004 | Brown | A61F 2/91 623/1.15 |
| 2004/0254637 A1* | 12/2004 | Yang | A61F 2/91 623/1.34 |
| 2006/0129045 A1* | 6/2006 | Warnack | A61F 2/958 600/435 |
| 2006/0241741 A1* | 10/2006 | Lootz | A61F 2/91 623/1.34 |
| 2007/0156230 A1* | 7/2007 | Dugan | A61F 2/91 623/1.16 |
| 2008/0009939 A1 | 1/2008 | Gueriguian et al. | |
| 2008/0215129 A1* | 9/2008 | Venturelli | A61F 2/91 623/1.11 |
| 2008/0243226 A1* | 10/2008 | Fernandez | A61F 2/91 623/1.15 |
| 2009/0204203 A1 | 8/2009 | Allen et al. | |
| 2010/0010622 A1* | 1/2010 | Lowe | A61F 2/91 623/1.16 |
| 2010/0070021 A1* | 3/2010 | Wack | A61F 2/915 623/1.16 |
| 2011/0198971 A1 | 8/2011 | Trollsas et al. | |
| 2011/0278771 A1* | 11/2011 | Kleiner | B29C 71/0063 264/479 |
| 2014/0094901 A1* | 4/2014 | Lorenzo | A61F 2/91 623/1.34 |

FOREIGN PATENT DOCUMENTS

| | | |
|---|---|---|
| JP | 2001516296 | 9/2001 |
| JP | 2009539486 | 11/2009 |
| WO | 9733534 | 9/1997 |
| WO | 9841384 | 9/1998 |
| WO | 2007105067 | 9/2007 |
| WO | 2007143279 | 12/2007 |

OTHER PUBLICATIONS

ISA to corresponding International Appl. No. PCT/EP2013/072239, 3 pages.

* cited by examiner

RADIOPAQUE MARKER FOR BIORESORBABLE STENTS

FIELD OF THE INVENTION

The present invention relates to a radiopaque marker and a method of applying the radiopaque marker to a vascular stent, in particular to a bioabsorbable or bioresorbable polymeric vascular stent.

BACKGROUND OF THE INVENTION

Many methods of medical imaging utilize high-energy electromagnetic radiations, such as X-rays, that can penetrate body tissues to create an image of internal structures, as well as implanted materials or tools that are inserted into the body. Common examples include X-ray imaging, fluoroscopy and computed axial tomography (a.k.a. CT or CAT scans). The ability to image structures and materials within the body depends in large part on the contrasting radiopacity of the different structures and materials. Radiopacity is the ability of a material to attenuate or block the passage of X-rays and other forms of electromagnetic radiation. Radiopacity of a material correlates closely with density and for a given material is proportional to the thickness. Often, a radiopaque dye, radiopaque filler material or radiopaque marker is used to enhance the radiopacity of structures or materials to make them more visible using X-ray imaging techniques. This is particularly important for imaging structures that are made of low density materials because they lack sufficient radiopacity to be visible by themselves using X-ray imaging techniques.

Polymer materials, such as those used in the making of polymeric vascular stents, generally have very low densities and therefore not enough radiopacity to be easily viewed inside the body using X-ray imaging techniques. The present invention concerns itself in particular with bioabsorbable or bioresorbable polymeric vascular stents. The terms bioabsorbable and bioresorbable are used interchangeably in the medical device industry to describe a material that, after implantation in the body, breaks down over time and is absorbed/resorbed by the surrounding tissues. Typical materials for bioabsorbable or bioresorbable stents include poly-lactic acid (PLA) and polyglycolic acid (PGA) polyglactin (PLAGA copolymer). Additional stent materials suitable for the present invention are described in U.S. Pat. No. 7,731, 740. Where allowed, this and all patents and patent applications referred to herein are hereby incorporated by reference. In general, a polymer with a glass transition temperature (Tg) of at least 45° C. or greater is preferred.

Some of the previous approaches to adding radiopacity or radiopaque markers to vascular stents are described in the following patents and patent applications: U.S. Patent Application 2007/0156230 Dugan, U.S. Pat. No. 6,293,966 Frantzen; U.S. Pat. No. 6,245,103 Stinson; U.S. Pat. No. 7,914,571 Calisse; U.S. Patent Application 2009/0204203 Allen; U.S. Pat. No. 8,127,422 Wu; U.S. Patent Application 2008/0009939 Gueriguian; EP 0894481 Stinson; U.S. Pat. No. 7,473,417 Zeltinger; U.S. Pat. No. 6,652,579 Cox; U.S. Pat. No. 6,174,330 Stinson; U.S. Pat. No. 6,368,346 Jadhav; U.S. Pat. No. 7,553,325 Stinson; U.S. Pat. No. 6,991,647 Jadhav; U.S. Pat. No. 7,951,194 Gueriguian; U.S. Pat. No. 6,464,723 Callol; U.S. Pat. No. 6,635,082 Hossainy; and U.S. Pat. No. 5,725,572 Lam.

Generally, the methods described in these patent references are not suitable for application to bioabsorbable or bioresorbable polymeric vascular stents. Therefore, it would be highly desirable to provide a radiopaque marker and a method of applying the radiopaque marker to a bioabsorbable or bioresorbable polymeric vascular stent.

BRIEF DESCRIPTION OF THE INVENTION

Figure 1:
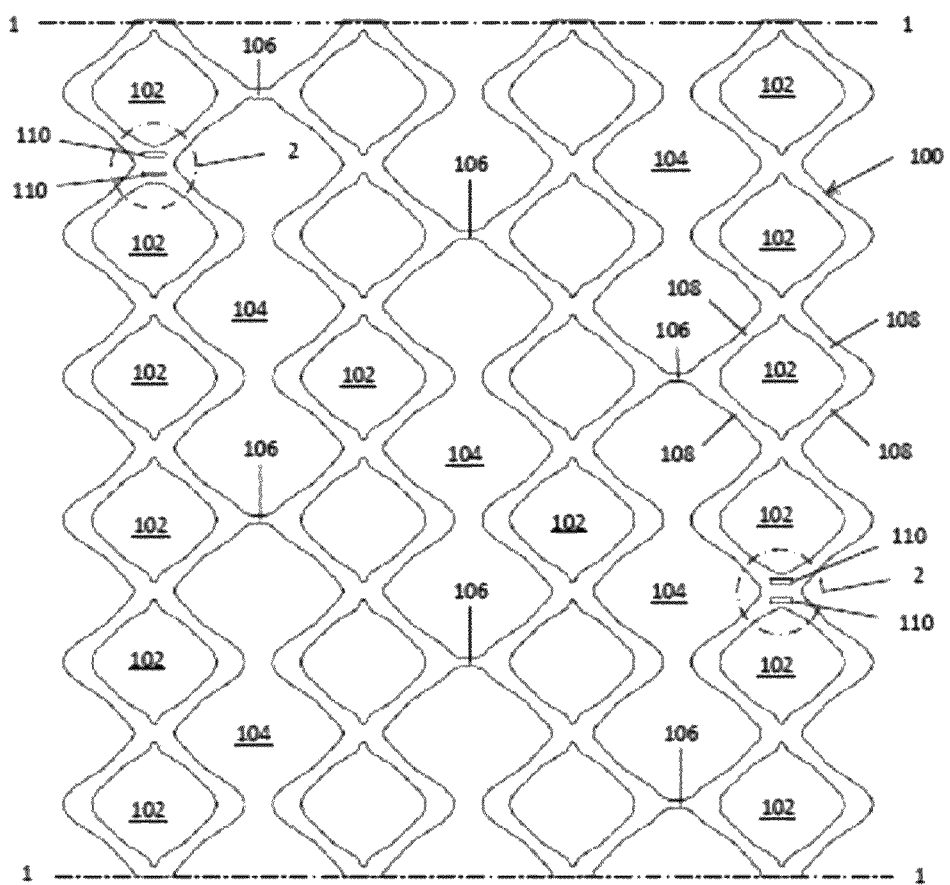
FIG. 1 illustrates a bioabsorbable or bioresorbable polymeric vascular stent laid out flat to show the structure of the stent and placement of slits for attaching a radiopaque marker.

Inventors herein provide a method of applying a radiopaque marker to a tubular stent. This method comprises:
forming a tubular stent with at least one opening through a wall of the tubular stent;
inserting a portion of a radiopaque marker into the opening in the wall of the tubular stent; and
heat treating the tubular stent to retain the portion of the radiopaque marker within the opening in the wall of the tubular stent.

The herein described method advantageously further comprises after the heat treating step, a step of cooling the tubular stent to a temperature below the glass transition temperature.

In a particular embodiment, the herein described method further comprises prior to the heat treating step, a step of placing an internal support rod into the tubular stent and a step of placing the tubular stent into an outer mold. The outer mold may advantageously comprise a lower half having at least one semicylindrical channel and an upper half having at least one semicylindrical channel.

In another particular embodiment, the at least one opening through a wall of the tubular stent comprises a pair of slits and the radiopaque marker preferably further comprises a pair of wall portions sized and configured to fit within the slits.

In a further particular embodiment, the radiopaque marker further comprises a roof portion joining together the pair of wall portions.

In another particular embodiment, the heat treating step of the tubular stent is to embed the radiopaque marker into the wall of the tubular stent In a preferred embodiment, the tubular stent is formed from a polymer having a glass transition temperature, typically from a bioresorbable polymer, preferably from a material comprising a poly (lactic acid) polymer, and wherein the heat treating step comprises heating the tubular stent to a temperature at or above the glass transition temperature.

Another object of the present invention is an apparatus comprising:
  a tubular stent having a stent wall constructed primarily of a polymeric material, preferably constructed of a bioresorbable polymeric material, and at least one slit formed in the stent wall; and
  a radiopaque marker constructed of a radiopaque material configured with a substantially flat roof portion and at least one wall portion extending from the roof portion; wherein the at least one wall portion of the radiopaque marker extends into the at least one slit formed in the stent wall and the at least one wall portion is gripped by the polymeric material surrounding the at least one slit.

In a particular embodiment of the present invention, the roof portion of the radiopaque marker is embedded into the stent wall of the tubular stent.

In another particular embodiment of the invention, the at least one slit comprises a pair of parallel slits formed in the stent wall and the at least one wall portion of the radiopaque marker preferably comprises a pair of parallel wall portions extending approximately perpendicular from the roof portion; the pair of wall portions of the radiopaque marker extending into the pair of slits formed in the stent wall and the pair of wall portions being gripped by the polymeric material surrounding the pair of slits. Preferably, the apparatus of the invention further comprises a second radiopaque marker constructed of a radiopaque material configured with a substantially flat roof portion and a pair of parallel wall portions extending approximately perpendicular from the roof portion; the pair of wall portions of the second radiopaque marker extending into a second pair of slits formed in the stent wall and the pair of wall portions of the second radiopaque marker being gripped by the polymeric material surrounding the second pair of slits.

In a particular embodiment, the radiopaque marker is positioned on an opposite end of the tubular stent and is diametrically opposed to the second radiopaque marker.

In a particular apparatus according to the present invention, i) the stent wall is constructed of a bioresorbable polymeric material having a glass transition temperature (Tg) of at least 45° C.; ii) the at least one slit comprises a pair of parallel slits formed in the stent wall and the at least one wall portion of the radiopaque marker comprises a pair of parallel wall portions extending approximately perpendicular from the roof portion; iii) the pair of wall portions of the radiopaque marker extends into the pair of slits formed in the stent wall and the pair of wall portions are gripped by the polymeric material surrounding the pair of slits; and iv) the roof portion of the radiopaque marker is embedded into the stent wall of the tubular stent.

DETAILED DESCRIPTION OF THE INVENTION

A radiopaque marker for a tubular stent is constructed of a radiopaque material and configured with a roof portion and a pair of wall portions extending approximately perpendicular to the roof portion. The radiopaque marker is applied to a tubular stent by a method including the steps of forming the tubular stent with a pair of openings through a wall of the tubular stent; inserting the wall portions of the radiopaque marker into the openings in the wall of the tubular stent; and heat treating the tubular stent to retain the wall portions of the radiopaque marker within the openings in the wall of the tubular stent. The heat treating step also embeds the roof portion of the radiopaque marker onto the wall of the tubular stent. The method of the invention is particularly adapted for applying a radiopaque marker to a bioresorbable polymeric vascular stent.

Figure 3:
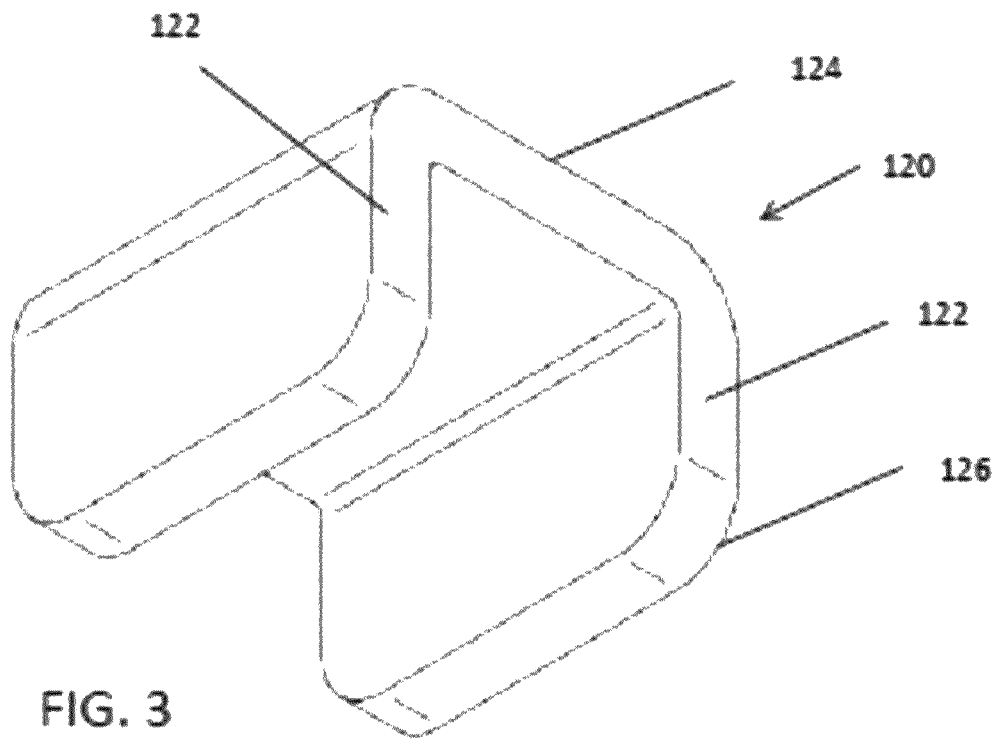
FIG. 3 is a perspective drawing of a radiopaque marker according to the present invention.
Figure 5:
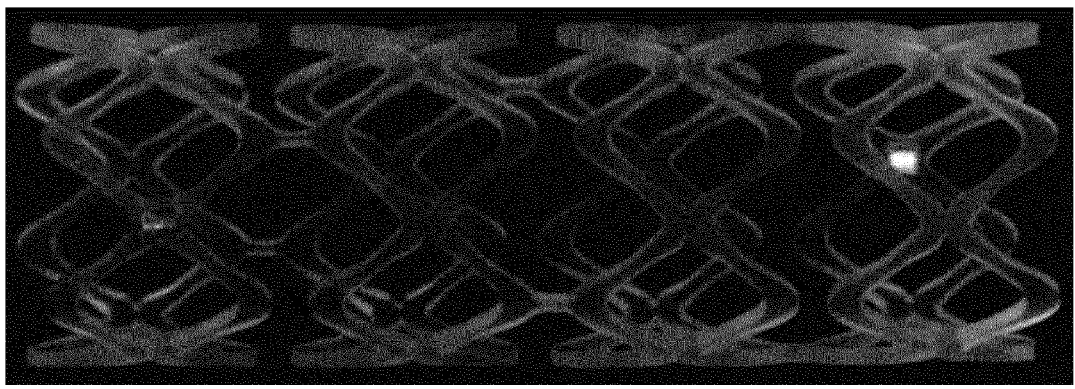
FIG. 5 is a photograph of a bioabsorbable or bioresorbable polymeric vascular stent having two radiopaque markers according to the present invention.

FIG. 1 illustrates a vascular stent 100 for use with a radiopaque marker 120 according to the present invention, which is shown in FIG. 3. Preferably, the stent 100 is made from a bioabsorbable or bioresorbable polymer having a glass transition temperature (Tg) of at least 45° C. The stent 100 is generally manufactured in a tubular configuration, but has been drawn as if it has been cut longitudinally along line 1-1 and laid out flat to more clearly illustrate the structure of the stent. FIG. 5 shows the finished stent 100 in its tubular configuration. The stent 100 can be manufactured in many different possible designs. This illustrative embodiment shows a stent 100 with a combination of closed cells 102 for structural strength in the circumferential direction (i.e. radial strength) and open cells 104 for flexibility in the longitudinal direction. Each of the closed cells 102 is bordered by four approximately-linear struts 108 whose ends are joined together to form a diamond, rhombus or lozenge-shaped cell 102. The illustrated stent 100 has six cells 102 in the circumferential direction and four cells 102 in the longitudinal direction. This stent configuration can be envisioned as having four circumferential rings with six closed cells 102 each, which are joined by two linking struts 106 between each pair of adjacent rings. Many other stent, cell and strut configurations are possible.

The stent 100 has a pair of slits 110 formed in it, for example by laser, waterjet, etching or machining, at preselected locations 2 for attachment of one or more radiopaque markers 120, as shown in FIG. 3. In this illustrative embodiment, one pair of slits 110 for a radiopaque marker 120 is located near a distal end of the stent 100 and another pair of slits 110 for a radiopaque marker 120 is located near a proximal end of the stent 100. The two radiopaque markers 120 will be located diametrically opposite one another when the stent is in a cylindrical configuration, as shown in FIG. 5. Many other arrangements of the radiopaque markers 120 are possible.

Figure 2:
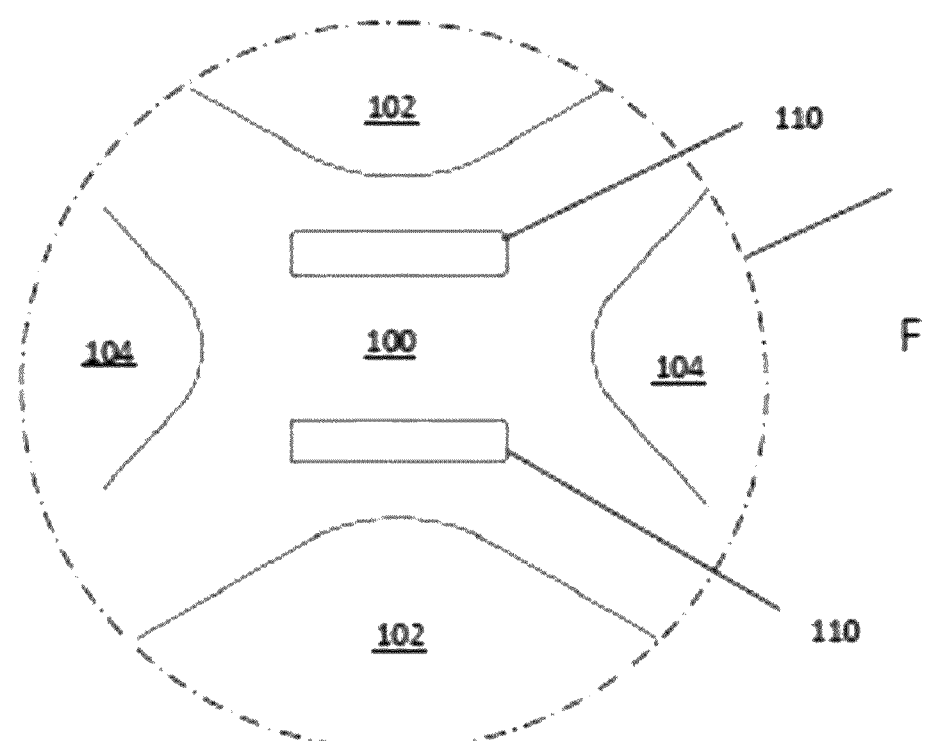
FIG. 2 is an enlarged detail drawing of a portion of the bioresorbable polymeric vascular stent of FIG. 1 showing the configuration of the slits for attaching a radiopaque marker.

FIG. 2 is an enlarged detail drawing of a portion 2 of the stent 100 of FIG. 1 showing the configuration of the slits 110 for attaching a radiopaque marker 120. Preferably, the pairs of slits 110 are each located at an X-shaped juncture between two adjacent cells 102 of the stent 100. The individual slits 110 are approximately rectangular and are positioned parallel to one another.

FIG. 3 is a perspective drawing of a radiopaque marker 120 according to the present invention. The radiopaque marker 120 is in approximately the shape of a flat-top arch with two wall portions 122 joined across the top by a roof portion 124. The bottom edges of the walls 122 preferably have raidused corners 126. The radiopaque marker 120 is preferably made of a high-density, biocompatible material. Suitable materials include, but are not limited to, gold, platinum, palladium, iridium, tungsten, tantalum, tin and mixtures, blends, alloys or composites thereof.

Alternatively, the radiopaque marker 120 can be made of a composite material, such as a polymer compounded with a high-density, biocompatible radiopaque filler material, for example barium sulfate ($BaSO_4$), bismuth trioxide ($Bi_2O_3$), bismuth subcarbonate ($Bi_2O_2CO_3$), bismuth oxychloride (BiOCl), tungsten (W) or tungsten carbide (WC) powder. As nonlimiting example, the roof portion 124 of the radiopaque marker 120 may have a length and width of approximately 300-500 microns and a thickness of approximately 25-50 microns. The height of the two wall portions 122 will depend in part upon the thickness of the stent 100. With the current bioresorbable stent design, the height of the two wall portions 122 may be approximately 100-300 microns. Other dimensions may be used to accommodate other stent designs.

The radiopaque markers 120 can be manufactures in a number of different ways. For example, a blank for a radiopaque marker 120 can be cut or punched from a sheet of radiopaque material of the desired thickness and then bent to the final shape. Alternatively, a channel of radiopaque material can be drawn or extruded through a shaped die and then cut to the desired length to form radiopaque markers 120. A sheet of radiopaque material of the appropriate thickness and width could also be drawn through a progressive shaping die to form a channel and then cut to the desired length to form radiopaque markers 120. Metal or polymer injection molding can be used to form radiopaque markers 120 in their final shape. Different shapes can also be accomplished. For example, a blank for a radiopaque marker 120 with a circular or other shape roof portion 124 and rectangular walls 122 can be cut or punched from a sheet of radiopaque material of the desired thickness and then bent to the final shape. As another example, injection molding can be used to form radiopaque markers 120 of many different shapes. Optionally, the radiopaque marker 120 can be made with one or more barbs, undercuts or protrusions on the vertical edges of the walls 122 to provide additional holding strength when attached to the stent 100.

For assembly to the stent 100, the walls 122 of the radiopaque marker 120 are inserted into the slits 110. Preferably, there is a sliding fit between the walls 122 of the radiopaque marker 120 and the sides of the slits 110 with enough friction to hold the radiopaque marker 120 in place at least temporarily while the next steps of the assembly process are performed. An extremely tight press fit is not necessary and might hinder assembly of the radiopaque marker 120 to the stent 100.

Figure 4:
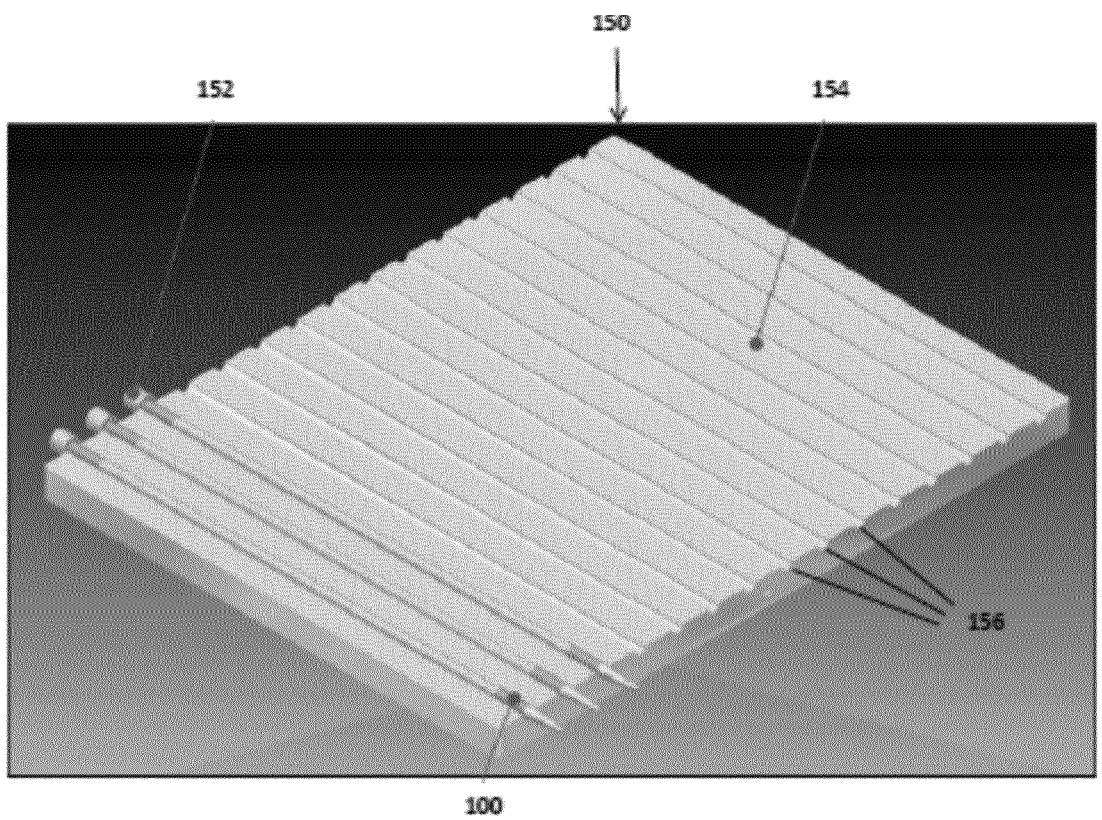
FIG. 4 is a perspective drawing of a heat treatment mold used in a method for applying the radiopaque marker to a bioabsorbable or bioresorbable polymeric vascular stent.

The stent 100 with the radiopaque markers 120 inserted into it is then heat treated to permanently attach the radiopaque markers 120 to the stent 100. FIG. 4 is a perspective drawing of a heat treatment mold 150 used in a method for applying the radiopaque markers 120 to the stent 100.

The heat treatment mold 150 includes an internal support rod or mandrel 152 and an outer mold 154.

The outer mold 154 is made with a lower half and an upper half (not shown), which have a plurality o semicylindrical channels 156 machined into them. The internal support rod 152 and the outer mold 154 are preferably made of a metal, such as stainless steel or aluminium, which allows for rapid heating and cooling of the heat treatment mold 150. Optionally, the internal support rod 152 and/or the outer mold 154 may be coated with a low-friction, heat-resistant material, such as PTFE. The internal support rod 152 is inserted into the lumen of the stent 100 and then the stent 100 and the internal support rod 152 are placed in one of the semicylindrical channels 156 in the lower half of the outer mold 154. When each of the semicylindrical channels 156 in the lower half of the outer mold 154 are filled, the upper half of the outer mold 154 is placed over the stents 100 and the internal support rods 152 and the heat treatment mold 150 is clamped closed.

Figure 6:
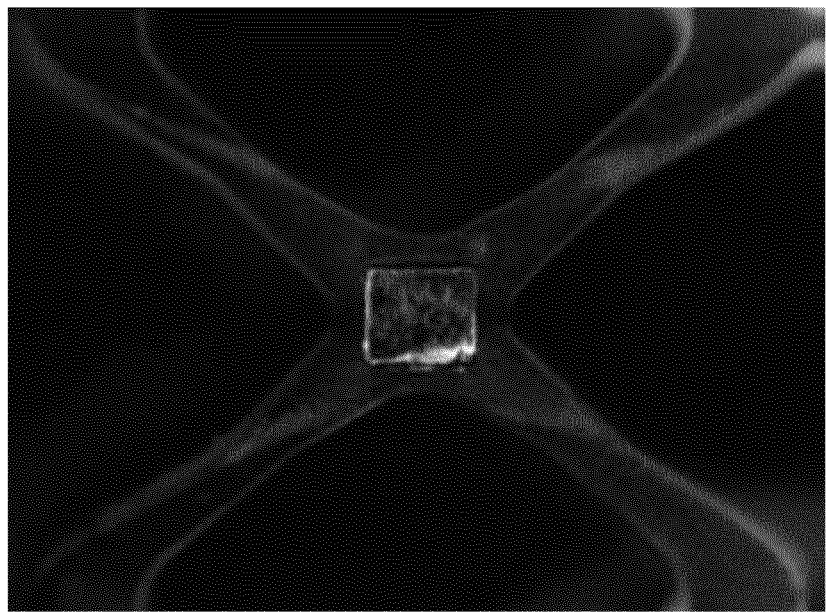
FIG. 6 is an enlarged detail photograph of a portion of the bioresorbable polymeric vascular stent of FIG. 5 showing one of the radiopaque markers.

The loaded heat treatment mold 150 is then placed in an oven at 45° C. or above to heat treat the stent 100. The heat treatment mold 150 constrains the stent 100 so that it is heat treated at its intended deployed diameter. After a predetermined heat treatment period, the heat treatment mold 150 is rapidly cooled to quench the stent material. Various heat treatment regimens are described in U.S. Pat. No. 7,731,740. After heat treatment, the slots 110 will be tightly gripping the walls 122 of the radiopaque marker 120 and the roof portion 124 of the radiopaque marker 120 will be embedded smoothly into the outer surface of the stent 100. FIG. 5 is a photograph of the completed vascular stent 100 with two radiopaque markers 120 constructed and assembled according to the present invention. FIG. 6 is an enlarged detail photograph of a portion of the vascular stent 100 of FIG. 5 showing one of the radiopaque markers 120.

Prior to use, the stent 100 is crimped onto an inflatable balloon of a stent delivery catheter. The catheter is inserted into the patient's vasculature to deliver the stent 100 to a stenosis or narrowing in an artery or other vessel. The balloon is inflated to expand the stent 100 and appose it to the vessel wall. The balloon is then deflated and the catheter is withdrawn. The expanded stent 100 holds open the previously stenosed portion of the artery. However, the material of the stent 100 gradually decomposes over a period of months and is resorbed by the surrounding tissues, thus allowing the artery to remodel and return to its normal function. The bioresorbable stent does not leave behind a large amount of foreign material that might cause inflammation, which could lead to restenosis or late stent thrombosis. Only the small radiopaque markers 120 are left in place, which serves as a fluoroscopic landmark so that the treated area of the vessel can be located during follow-up angiograms. Precious metal radiopaque markers, such as gold or platinum-series metals, are extremely biocompatible and do not pose a danger of causing inflammation.

Optionally, the bioresorbable stent may include an antiproliferative agent, such as paclitaxel, sirolimus (rapamycin) or another limus-family drug, in the form of a coating or compounded into the polymer for extended release.

The invention claimed is:

1. A method of applying a radiopaque marker to a bioresorbable polymeric tubular stent, the method comprising:
    forming a tubular stent with at least one opening through a wall of the tubular stent, the wall of the tubular stent being constructed of a bioresorbable polymeric material and the at least one opening comprising a pair of slits;
    inserting a portion of a radiopaque metal marker into the opening in the wall of the tubular stent wherein the radiopaque metal marker comprises a pair of wall portions sized and configured to fit within the slits and a roof portion joining together the pair of wall openings; and then
    heat treating the tubular stent to retain the portion of the radiopaque marker within the opening in the wall of the tubular stent, wherein the heat treating step embeds the walls and the roof portion of the radiopaque marker into the wall of the tubular stent.

2. The method of claim 1, wherein the tubular stent is formed from a polymer having a glass transition temperature and wherein the heat treating step comprises heating the tubular stent to a temperature at or above the glass transition temperature.

3. The method of claim 1, further comprising after the heat treating step, cooling the tubular stent to a temperature below the glass transition temperature.

4. The method of claim 1, wherein the tubular stent comprises a poly (lactic acid) polymer.

5. The method of claim 1, further comprising prior to the heat treating step, placing an internal support rod into the tubular stent and placing the tubular stent into an outer mold.

6. The method of claim 5, wherein the outer mold comprises a lower half having at least one semicylindrical channel and an upper half having at least one semicylindrical channel.

7. The method of claim 1 wherein the pair of slits is located at an X-shaped juncture between two adjacent cells of the stent.

8. A tubular stent directly obtained with a method according to claim 1.

* * * * *